United States Patent [19]
Sauer et al.

[11] Patent Number: 5,658,236
[45] Date of Patent: *Aug. 19, 1997

[54] OPTICAL TROCAR

[75] Inventors: Jude S. Sauer, Pittsford; Michael G. Oravecz, Rochester; Roger J. Greenwald, Holley; Alexander I. Kobilansky, Pittsford, all of N.Y.

[73] Assignee: United States Surgical Corporation, Norwalk, Conn.

[ * ] Notice: The portion of the term of this patent subsequent to Sep. 13, 2013, has been disclaimed.

[21] Appl. No.: 408,419

[22] Filed: Mar. 21, 1995

Related U.S. Application Data

[63] Continuation of Ser. No. 120,489, Sep. 13, 1993, Pat. No. 5,441,041.

[51] Int. Cl.$^6$ .................................................. A61B 1/04
[52] U.S. Cl. ..................... 600/114; 600/105; 604/164; 606/185
[58] Field of Search ........................... 606/185, 167, 606/170, 1, 2, 10, 11, 12, 13, 14, 15, 16; 600/104, 114, 117, 127, 138, 105, 106; 604/164, 264, 165, 166, 272

[56] References Cited

U.S. PATENT DOCUMENTS

| | | |
|---|---|---|
| 1,380,447 | 6/1921 | Wescott . |
| 1,727,495 | 9/1929 | Wappler . |
| 2,699,770 | 1/1955 | Fourestier et al. . |
| 2,764,148 | 9/1956 | Sheldon . |
| 2,764,149 | 9/1956 | Sheldon . |
| 2,877,368 | 3/1959 | Sheldon . |
| 3,021,834 | 2/1962 | Sheldon . |
| 3,417,745 | 12/1968 | Sheldon . |
| 3,437,747 | 4/1969 | Sheldon . |
| 3,499,107 | 3/1970 | Sheldon . |
| 3,538,916 | 11/1970 | Wiles . |
| 3,556,085 | 1/1971 | Takahashi . |
| 3,762,416 | 10/1973 | Moss et al. . |
| 3,809,095 | 5/1974 | Cimber . |
| 3,915,169 | 10/1975 | McGuire . |
| 3,961,621 | 6/1976 | Northeved . |
| 4,210,146 | 7/1980 | Banko . |
| 4,220,155 | 9/1980 | Kimberling et al. . |
| 4,254,762 | 3/1981 | Yoon . |
| 4,256,119 | 3/1981 | Gauthier . |
| 4,269,192 | 5/1981 | Matsuo . |

(List continued on next page.)

FOREIGN PATENT DOCUMENTS

| | | |
|---|---|---|
| 135364 | 3/1985 | European Pat. Off. . |
| 0433581 | 6/1991 | European Pat. Off. . |
| 0484725 | 5/1992 | European Pat. Off. . |
| 0604197 | 6/1994 | European Pat. Off. . |
| 1616107 | 11/1971 | Germany . |
| 2538758 | 3/1977 | Germany . |
| 2800607 | 10/1978 | Germany . |
| 2922239 | 3/1982 | Germany . |
| 9112976 | 12/1991 | Germany . |
| 4133073 | 4/1992 | Germany . |
| 4035146 | 5/1992 | Germany . |
| 537677 | 12/1976 | U.S.S.R. . |
| 942730 | 7/1982 | U.S.S.R. . |
| 719538 | 12/1954 | United Kingdom . |
| 1215383 | 12/1970 | United Kingdom . |
| 2048686 | 12/1980 | United Kingdom . |
| 9214514 | 9/1992 | WIPO . |

OTHER PUBLICATIONS

European Search Report dated Dec. 7, 1994.

*Primary Examiner*—Beverly M. Flanagan

[57] ABSTRACT

The present invention relates to an optical obturator which includes a sleeve having a longitudinal bore between a proximal end and a distal end. The longitudinal bore of the sleeve is configured to receive at least a portion of an endoscope or like image transferring system. An image directing member is positioned at the distal end of the sleeve and is provided to direct optical images into the longitudinal bore of the sleeve. A movable blade is positioned distal to the image directing member to facilitate penetration of body tissue.

14 Claims, 4 Drawing Sheets

U.S. PATENT DOCUMENTS

| | | |
|---|---|---|
| 4,345,589 | 8/1982 | Hiltebrandt . |
| 4,411,653 | 10/1983 | Razi . |
| 4,461,305 | 7/1984 | Cibley . |
| 4,516,575 | 5/1985 | Gerhard et al. . |
| 4,535,773 | 8/1985 | Yoon . |
| 4,539,976 | 9/1985 | Sharpe . |
| 4,559,041 | 12/1985 | Razi . |
| 4,566,438 | 1/1986 | Liese et al. . |
| 4,570,632 | 2/1986 | Woods . |
| 4,653,475 | 3/1987 | Seike et al. . |
| 4,667,684 | 5/1987 | Leich . |
| 4,723,545 | 2/1988 | Nixon et al. . |
| 4,733,671 | 3/1988 | Mehl . |
| 4,790,312 | 12/1988 | Capuano, Sr. et al. . |
| 4,865,029 | 9/1989 | Pankratov et al. . |
| 4,904,246 | 2/1990 | Atkinson . |
| 4,957,112 | 9/1990 | Yokoi et al. . |
| 4,961,414 | 10/1990 | Cho et al. . |
| 4,962,770 | 10/1990 | Agee et al. . |
| 4,976,269 | 12/1990 | Mehl . |
| 4,991,600 | 2/1991 | Taylor . |
| 5,066,288 | 11/1991 | Dehiega et al. . |
| 5,089,000 | 2/1992 | Agee et al. . |
| 5,092,872 | 3/1992 | Segalowitz . |
| 5,104,382 | 4/1992 | Brinkeroff et al. . |
| 5,116,353 | 5/1992 | Green . |
| 5,146,921 | 9/1992 | Terwilliger et al. . |
| 5,152,754 | 10/1992 | Plyley et al. . |
| 5,158,552 | 10/1992 | Borgia et al. . |
| 5,159,920 | 11/1992 | Condon et al. . |
| 5,176,695 | 1/1993 | Dulebohn . |
| 5,183,053 | 2/1993 | Yeh et al. . |
| 5,186,178 | 2/1993 | Yeh et al. . |
| 5,250,068 | 10/1993 | Ideguchi et al. . |
| 5,271,380 | 12/1993 | Riek et al. . |
| 5,275,583 | 1/1994 | Crainich . |
| 5,314,417 | 5/1994 | Stephens et al. . |
| 5,334,150 | 8/1994 | Kaali . |
| 5,354,302 | 10/1994 | Ko . |
| 5,372,588 | 12/1994 | Farley et al. . |
| 5,385,572 | 1/1995 | Nobles et al. . |
| 5,406,940 | 4/1995 | Melzer et al. . |

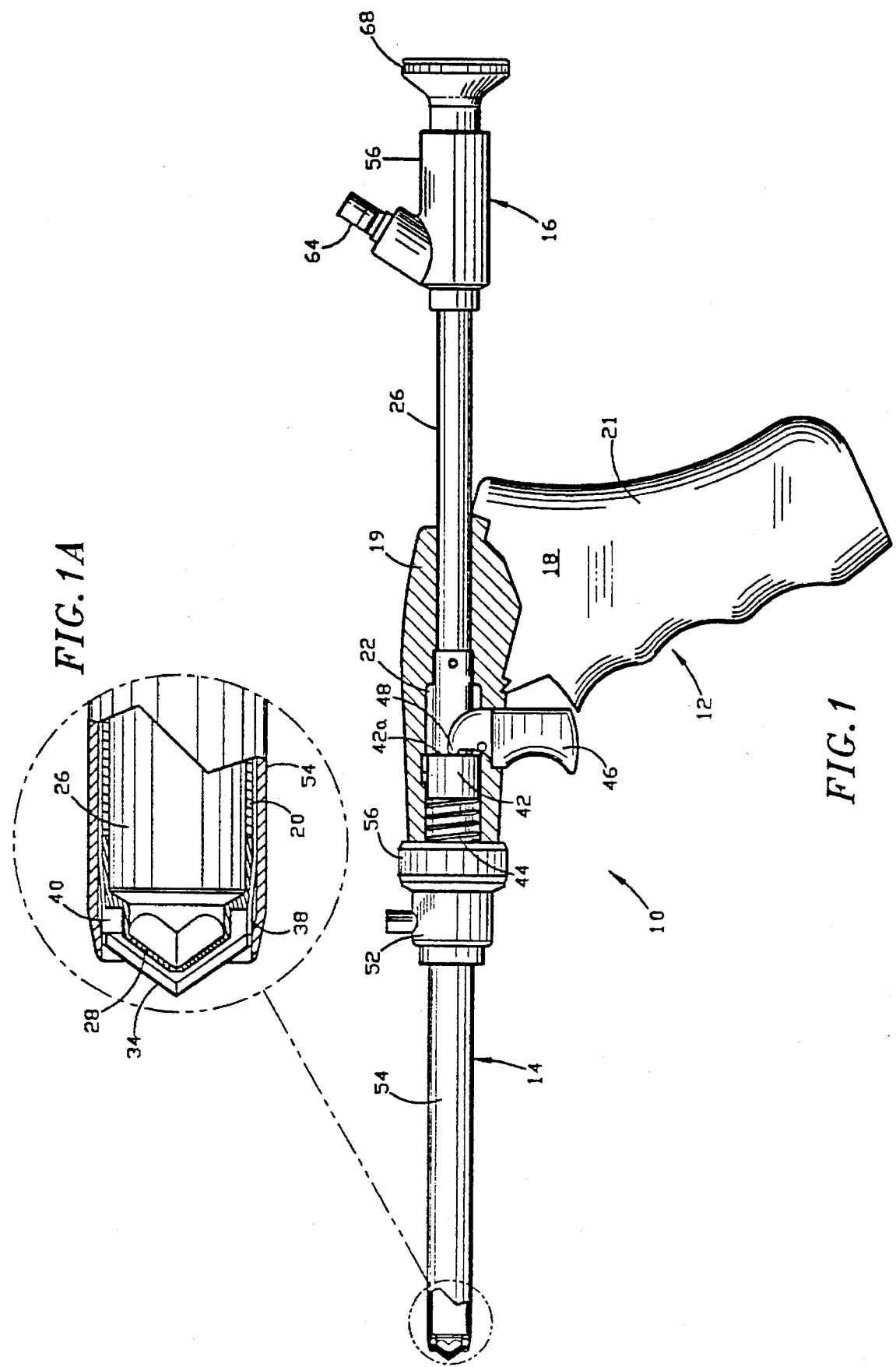

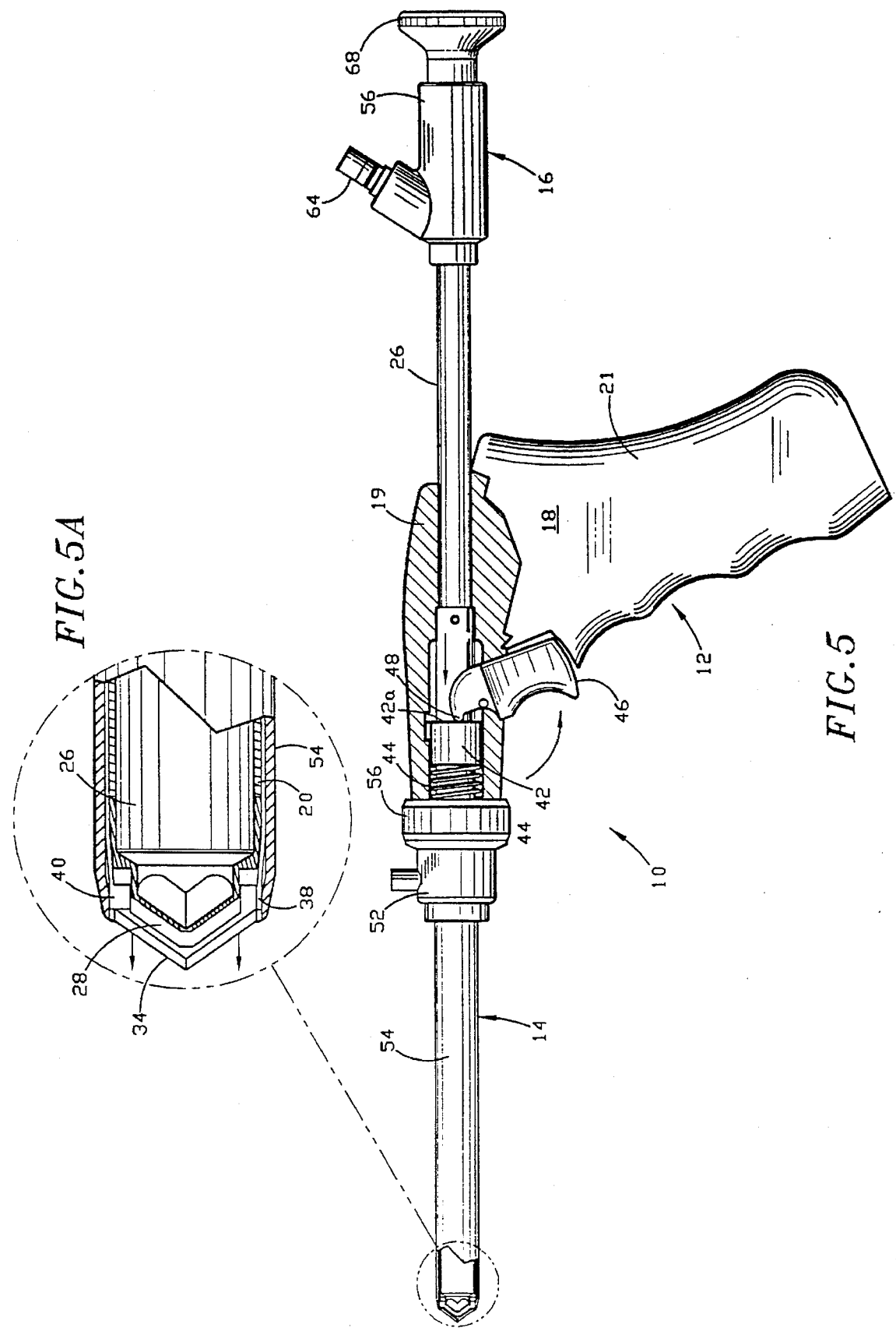

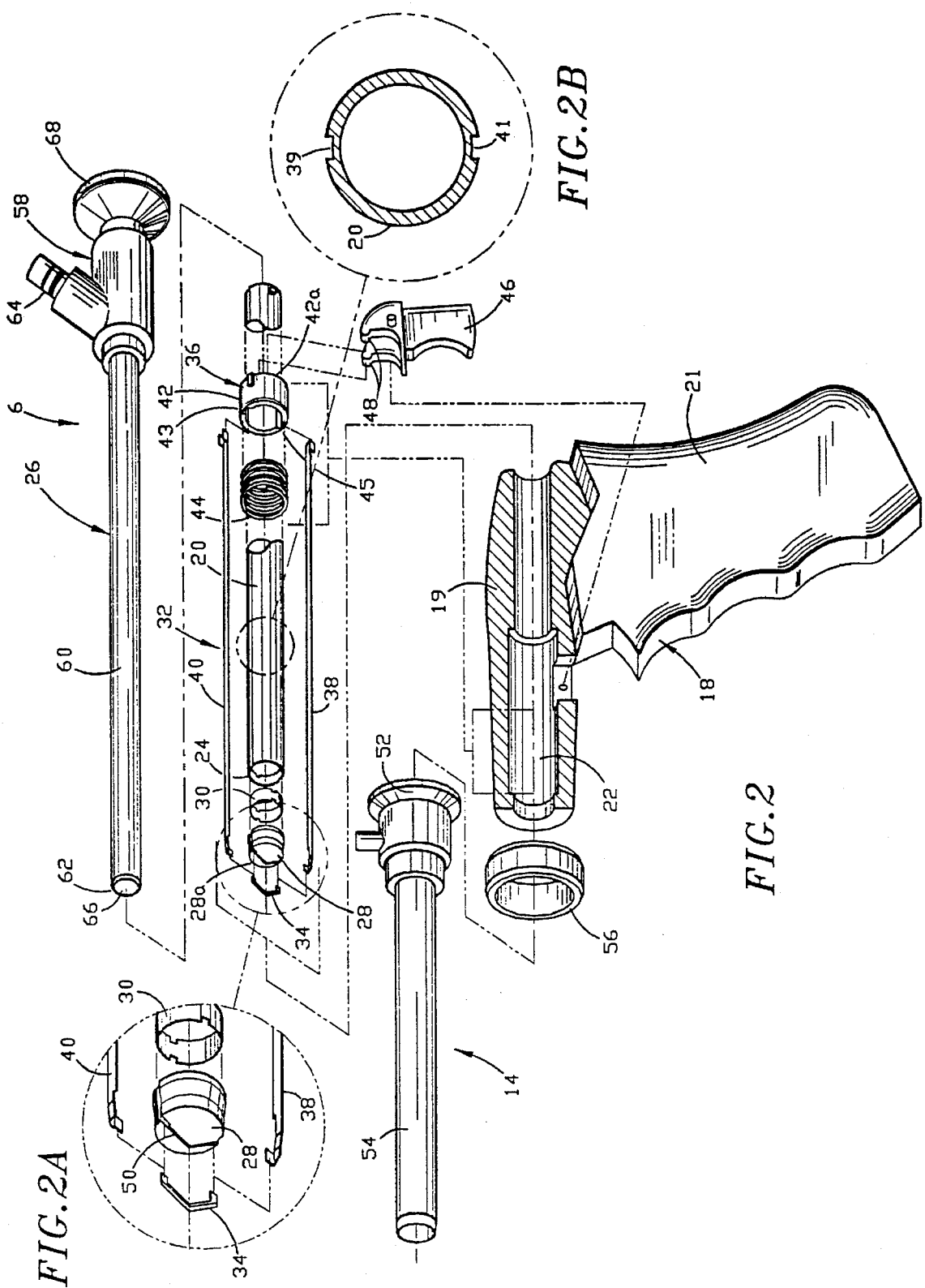

OPTICAL TROCAR

This is a continuation of U.S. application Ser. No. 08/120,489 filed Sep. 13, 1993, now U.S. Pat No. 5,441,041.

BACKGROUND OF THE INVENTION

1. Field of the Invention

The present invention relates to an apparatus for penetrating and for observing penetration of body tissue. More particularly, the present invention relates to a trocar assembly having an endoscope or laparoscope inserted therethrough to provide visual observation during penetration of the peritoneum or other body tissue.

2. Description of the Related Art

Endoscopic surgical procedures, that is, surgical procedures performed through tubular sleeves or cannulas, have been utilized for many years. Initially, endoscopic surgical procedures were primarily diagnostic in nature. More recently as endoscopic technology has advanced, surgeons are performing increasingly complex and innovative endoscopic surgical procedures. In endoscopic procedures, surgery is performed in any hollow viscus of the body through a small incision or through narrow endoscopic tubes (cannulas) inserted through small entrance wounds in the skin. In laparoscopic procedures surgery is performed in the interior of the abdomen.

Laparoscopic procedures generally utilize instrumentation that is internally sealed to inhibit gases from entering or exiting the body through the laparoscopic or endoscopic incision. This is particularly true in surgical procedures in which the surgical region is insufflated. Moreover, laparoscopic and endoscopic procedures often require the surgeon to act on organs, tissues and vessels far removed from the incision, thereby requiring that any instruments to be used in such procedures be of sufficient size and length to permit remote operation. Typically, after the surgical region is insufflated, trocars are used to puncture the body cavity and include a cannula which remains in place for use during endoscopic procedures. Generally, trocars used during such procedures include a stylet having a sharp tip for penetrating the body cavity positioned coaxially within protective tubes to protect a patient or surgeon from inadvertent contact with the tip. An example of a known trocar is described in commonly assigned, U.S. Pat. No. 4,601,710 to Moll. Most currently used trocars rely on protective tubes or relative retraction of the tip to prevent inadvertent contact with tissue.

The present invention provides a trocar assembly for observing the penetration of the peritoneum or other body portions. The trocar assembly of the present invention provides an improved structure for directing optical images which provides a clear and bright image of the body tissue being penetrated. In addition, the present invention provides an improved cutting tip for penetration of body tissue.

SUMMARY OF THE INVENTION

The present invention relates to an optical obturator which includes a sleeve having a longitudinal bore between a proximal end and a distal end. The longitudinal bore of the sleeve is configured to receive at least a portion of an endoscope or like image transferring system. An image directing member is positioned at the distal end of the sleeve and is provided to direct optical images into the longitudinal bore of the sleeve. A movable blade is positioned distal to the image directing member to facilitate penetration of body tissue.

The present invention also provides a trocar which includes a cannula assembly, an obturator assembly and an image transferring system. The cannula assembly includes a cannula housing and a cannula sleeve extending from said cannula housing. The obturator assembly includes an obturator sleeve having a proximal end, a distal end and a longitudinal bore therebetween which are configured for coaxial alignment with the cannula assembly.

An image directing member is positioned at the distal end of the obturator sleeve and is provided to direct optical images into the longitudinal bore of the sleeve. A tissue penetrating member, such as a blade, is positioned adjacent the distal end of the obturator sleeve and distal to the image directing means and is preferably movable between non-deployed and deployed positions. Preferably, the tissue penetrating member is configured to facilitate observation of body tissue simultaneous with penetration of body tissue.

In the preferred embodiment, the image directing member includes a prism having four substantially flat surfaces for receiving optical images. Alternatively, the image directing means includes a lens having at least one conical surface for receiving optical images.

The present invention also provides an apparatus for simultaneous observation of penetration of body tissue which includes a cannula assembly having a cannula housing and a cannula sleeve extending from the cannula housing. Typically, the cannula sleeve has a longitudinal bore extending from a proximal end to a distal end. An obturator assembly having an obturator housing and an obturator sleeve is provided to interfit with the cannula assembly. A distal end of the obturator sleeve has an image directing member secured thereto configured to direct optical images into the bore of the obturator sleeve. The apparatus also includes tissue penetrating means positioned distal to the image directing member and movable between non-deployed and deployed positions. In addition, image transferring means, such as an endoscope, is positioned within the longitudinal bore of the obturator sleeve and is provided to transmit optical images from the image directing member to a proximal end of the obturator housing for subsequent viewing by the surgeon.

BRIEF DESCRIPTION OF THE DRAWINGS

The preferred embodiments of the invention are described hereinbelow with reference to the drawings wherein:

FIG. 1 is a side elevational view in partial cross-section of the apparatus according to the present invention, illustrating an endoscope positioned within a trocar assembly having a movable cutting blade;

FIG. 1A is an enlarged partial cross-sectional view of the distal end of the apparatus of FIG. 1, illustrating the cutting blade in a non-deployed position;

FIG. 2 is an exploded perspective view of the instrument of FIG. 1 with parts separated, illustrating an actuating assembly for moving the cutting blade;

FIG. 2A is an exploded perspective view of an image directing member and blade according to the present invention;

FIG. 2B is a cross-sectional view of the obturator sleeve of the present invention;

FIG. 5 is a side elevational view similar to FIG. 1, illustrating actuation of the trigger assembly to move the blade to a deployed position; and

3

Figure 4:
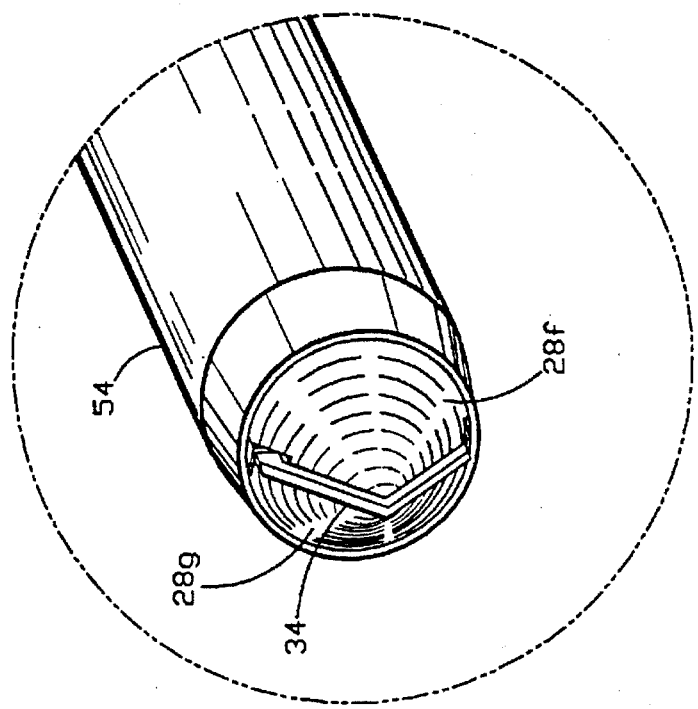
FIGS. 3 and 4 illustrate alternative embodiments for the configuration of the image directing member according to the present invention.

FIG. 5A is an enlarged partial cross-sectional view 10 of the distal end of the apparatus of FIG. 5, illustrating the cutting blade in the deployed position.

DETAILED DESCRIPTION OF THE PREFERRED EMBODIMENTS

The apparatus of the present invention is provided to penetrate body tissue, e.g., the abdominal wall, and to provide a simultaneous forward directional view of the body tissue being penetrated. In the preferred embodiment, the apparatus includes a trocar assembly 10 having an obturator assembly 12 and a cannula assembly 14, and an endoscope 16 which is positioned within the obturator assembly to provide observation of the body tissue being penetrated.

Referring to FIGS. 1 and 2, obturator assembly 12 includes housing 18 and a longitudinally extending obturator sleeve 20. Preferably, obturator housing 18 includes barrel portion 19 and hand grip 21. The proximal end of obturator sleeve 20 is secured within channel 22 of barrel portion 19 so that the obturator sleeve 20 extends outwardly from the obturator housing 14. Hand grip 21 is provided for manual gripping to facilitate penetration of the body tissue. Obturator sleeve 20 has a longitudinal bore 24 which extends between the proximal end and distal end. The longitudinal bore 24 is configured and dimensioned to receive the endoscopic portion 26 of the endoscope 16, as shown in FIG. 1.

Figure 3:
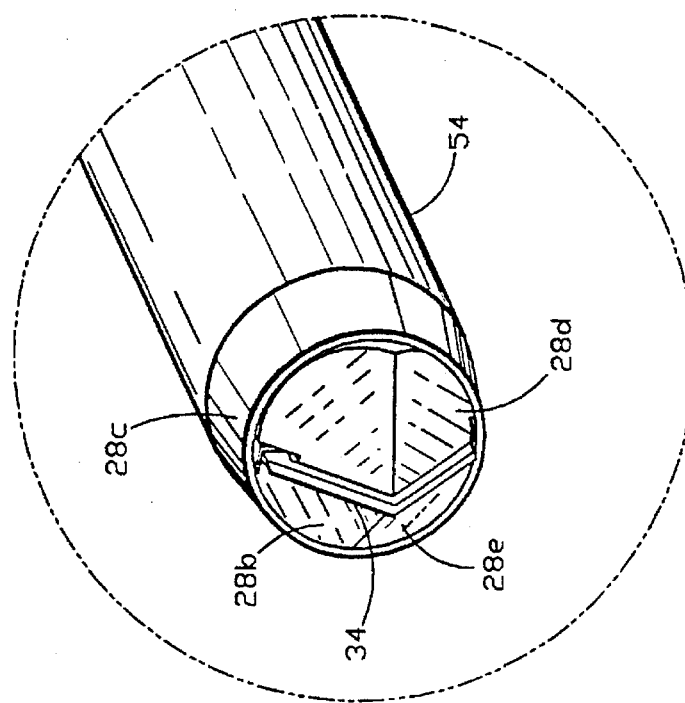

Referring to FIGS. 2, 3 and 4, image directing member 28 is secured to the distal end of obturator sleeve 20 via retaining ring 30. In this configuration, optical images which impinge the distal end 28a of image directing member 28 are directed into longitudinal bore 24 of obturator sleeve 20. The image directing member may be a lens, an optical prism, an optical mirror, or like image directing medium and is preferably configured to allow a 360° forward angle of view. In the preferred embodiment, image directing member 28 is a prism which includes a set of four substantially flat surfaces 28b, 28c, 28d and 28e, as shown in FIG. 3. The flat surfaces direct the optical image into the longitudinal bore of the obturator sleeve so as to provide a clear image. Alternatively, the image directing member is a lens which includes a set of two conical surfaces 28f and 28g which direct an optical image into the longitudinal bore 24 of obturator sleeve 20 (see FIG. 4).

Referring again to FIG. 2, the cutting portion 32 of obturator assembly 12 includes a cutting blade 34 connected to actuating assembly 36. Actuating assembly 36 is provided to move blade 34 between a non-deployed position (FIG. 1A) and a deployed position (FIG. 5A) which will be described in more detail below. The cutting blade 34 is preferably centered with respect to the outer surface of the image directing member as shown. Thus, in visulization, the cutting blade is seen as a thin line through the center, i.e. bisecting, the viewing field so as not to obstruct viewing of the body.

Actuating assembly 36 includes blade pusher arms 38 and 40, blade drive member 42, drive spring 44 and trigger 46. Blade 34 is connected such as by welding, to the distal end of blade pusher arms 38 and 40 which extend along the longitudinal axis of obturator sleeve 20 within slots 39 and 41 in obturator sleeve 20, shown in FIG. 2B. The proximal end of blade pusher arms 38 and 40 are secured within slots 43 and 45 of blade drive member 42, as shown. Blade drive member 42 and drive spring 44 are positioned within channel 22 of obturator housing 18 so that drive spring 44 normally biases blade drive member 42 toward the proximal end of obturator housing 18, thus biasing blade 34 to the proximal non-deployed position.

Trigger 46 is pivotally secured to obturator housing 18 via pin 47, as shown, so that camming surface 48 of trigger 46 engages the proximal end portion 42a of blade drive member 42. Thus, actuation of trigger 46, i.e. movement in the direction of the arrow in FIG. 5, causes camming surface 48 to engage blade drive member 42 and move the drive member distally within channel 22. Distal movement of drive member 42 causes blade pusher arms 38 and 40 to move distally to move blade 34 distally to the deployed (extended) position. Release of trigger 46 permits blade 34 to return to the non-deployed position in response to the action of drive spring 48 forcing blade drive member 42 proximally.

The movement of blade 34 between non-deployed and deployed positions can be seen by comparing FIGS. 1 and 5. As shown in FIGS. 1 and 1A, in the non-deployed position the blade 34 is at rest within recess 50 (FIG. 2A) in image directing member 28. In the deployed position blade 34 is extended from recess 50 beyond the distal end of cannula assembly 14, as shown in FIG. 5.

With reference to FIG. 2, cannula assembly 14 includes cannula housing 52 and cannula sleeve 54 secured to the cannula housing 52 and extending outwardly therefrom. Obturator housing 18 includes bushing 56 which is configured and dimensioned to interfit with the proximal end of cannula housing 52, as shown in FIG. 1, so that obturator sleeve 20 coaxially aligns with cannula sleeve 54 when the two assemblies are interfitted. The cannula sleeve 54 is adapted to remain in the body after penetration and subsequent removal of the obturator assembly 12 (and endoscope 10) to allow insertion of appropriate endoscopic/laparoscopic instrumentation therethrough.

To maintain a gas tight seal within the cannula housing, a sealing member or system may be positioned therewithin which is adapted to receive the obturator assembly 12 of the present invention as well as other endoscopic surgical instruments. One example of a suitable sealing system utilizes a duckbill sealing member. A more detailed description of an exemplary cannula assembly and sealing system is found in U.S. Pat. No. 5,180,373 issued Jan. 19, 1993, which is incorporated herein by reference.

Referring to FIGS. 1A and 2, endoscope 16 includes endoscopic portion 26 and endoscope housing 58. Endoscopic portion 26 is configured to transfer illuminating light from endoscope housing 58 to the distal end of the endoscopic portion to provide illuminating light to the operative site. In an exemplary configuration, endoscopic portion 26 includes an outer sheath 60 and an annular array of fiber optic elements 62 extending between light source connector 64 of endoscope housing 58 and the distal end of outer sheath 60 to illuminate the operative site. Any known light source may be connected to connector 64 to provide the illuminating light. In addition, endoscopic portion 26 includes an image transferring system 66 which may include a bundle of fiber Optic elements or objective lenses which transfer an optical image to eyepiece 68 for viewing. Alternatively, a video system including a monitor may be operatively connected to housing 58 to provide a video image of the body tissue being penetrated. Preferably, the fiber optic elements 62 are positioned adjacent the inner wall of the outer sheath so as to surround the image transferring system. In this configuration, optical images which impinge on the image directing member 28 are directed into the image transferring system and relayed to eyepiece 68. An example of an endoscope which can be utilized is described in U.S. Pat. No. 4,964,710 incorporated herein be reference.

In operation, endoscope 16 is inserted into the trocar assembly 10, i.e. into longitudinal bore 24 of obturator sleeve 20, as shown in FIG. 1. The surgeon then positions the blade 34 against the body tissue and may continuously move blade 34 between the non-deployed and deployed positions, i.e., reciprocally moving blade 34, via actuating assembly 32. Pressure is applied to hand grip 21 in the distal direction to penetrate the body tissue. The movement of blade 34 facilitates cutting of the body tissue, thus permitting the surgeon to apply minimal pressure to hand grip 21 to penetrate the body tissue.

During penetration of the body tissue the surgeon either observes such penetration through eyepiece 68, or in instances where a video system is utilized the surgeon simply observes the penetration of the body tissue via any known video monitor.

Once the surgeon penetrates the body tissue as observed through endoscope 16, the surgeon releases trigger 46 to permit blade 34 to return to the non-deployed position and discontinues application of pressure to hand grip 21.

In operation, the surgeon may also more selectively deploy the blade 34 during penetration. That is, the surgeon may insert the trocar assembly and bluntly penetrate the body tissue until reaching thicker tissue, such as muscle. At this point, the blade can be deployed to penetrate (cut through) this thick tissue, then retracted to provide blunt penetration until thick tissue is again encountered where once again the blade can be deployed.

After penetration into the body cavity, both the endoscope 16 and the obturator assembly 12 are removed from the cannula assembly 14, leaving the cannula assembly 14 in the body for insertion of desired instrumentation therethrough.

In an alternate embodiment, the obturator assembly 12 and endoscope 16 or optical components thereof can be a single unit inserted into cannula assembly 14. For example, the obturator assembly can be manufactured with illumination optics and/or imaging optics positioned therein so that the obturator assembly itself can function to penetrate tissue as well as to light the surgical site and transmit images to the video monitor. In this version, the obturator would not have a longitudinal bore and it would be sealed.

It will be understood that various modifications can be made to the embodiments of the present invention herein disclosed without departing from the spirit and scope thereof. For example, various diameters for the cannula assembly, the obturator assembly, as well as various diameter endoscopes are contemplated. Also, various modifications may be made in the configuration of the parts. Therefore, the above description should not be construed as limiting the invention but merely as exemplifications of preferred embodiments thereof. Those skilled in the art will envision other modifications within the scope and spirit of the present invention as defined by the claims appended hereto.

What is claimed is:

1. An apparatus comprising:

a) an outer sleeve member having a seal and a longitudinal bore extending therethrough, the longitudinal bore dimensioned to receive endoscopic instruments therethrough;

b) an inner sleeve member removably positioned in the outer sleeve, the inner sleeve having a proximal end and a distal end and including:

i) a bore dimensioned to receive an endoscope;
        ii) a recess formed in a distal end;
        iii) a cutting blade movably positioned at the distal end;
        iv) an actuator positioned at the proximal end and operatively connected to the cutting blade, the actuator selectively moving the cutting blade between a retracted position and an extended position with respect the recess; and
        v) an image directing member positioned at the distal end, the image directing member directing images into the bore of the inner sleeve member when the endoscope is positioned in the bore.

2. The apparatus of claim 1, wherein the actuator includes a trigger movable in a proximal direction to move the cutting blade to the extended position.

3. The apparatus of claim 2, wherein the image directing member is a prism including four substantially flat surfaces.

4. The apparatus of claim 3, wherein the image directing member is a lens which includes a set of two conical surfaces.

5. The apparatus of claim 2, further comprising a pair of elongated blade arms operatively connecting the cutting blade and trigger.

6. The apparatus of claim 5, further comprising a spring biasing the cutting blade to the retracted position.

7. In combination an endoscope, an apparatus for receiving the endoscope, and a cannula assembly for receiving the apparatus, the apparatus comprising:

a) a sleeve member having a outer dimension sized for reception in an opening in the cannula assembly, the sleeve member including a bore dimensioned to receive the endoscope and terminating at its distal end in an image directing member, the image directing member having a recess formed therein to receive a cutting blade;

b) a cutting blade movably positioned with respect to the image directing member; and c) an actuator positioned at the proximal end of the sleeve member and operatively connected to the cutting blade, the actuator selectively moving the cutting blade from a retracted position positioned in the recess to an extended position at least partially extending from the recess.

8. The combination of claim 7, wherein the actuator includes a trigger movable in a proximal direction to move the cutting blade to the extended position.

9. The combination of claim 7, wherein the image directing member is a prism including four substantially flat surfaces.

10. The combination of claim 7, wherein the image directing member is a lens which includes a set of two conical surfaces.

11. The combination of claim 8, further comprising a pair of elongated blade arms operatively connecting the cutting blade and trigger.

12. The combination of claim 11, further comprising a spring biasing the cutting blade to the retracted position.

13. The combination of claim 7, wherein the cannula assembly includes a cannula housing, a cannula sleeve and a seal in the cannula housing.

14. The combination of claim 7 wherein the endoscope includes a bundle of fiber optic elements or objective lenses.

* * * * *